US010324026B2

(12) United States Patent
Chapuis

(10) Patent No.: US 10,324,026 B2
(45) Date of Patent: Jun. 18, 2019

(54) TESTING OF AN INDUSTRIAL STRUCTURE

(71) Applicant: COMMISSARIAT A L'ENERGIE ATOMIQUE ET AUX ENERGIES ALTERNATIVES, Paris (FR)

(72) Inventor: Bastien Chapuis, Viroflay (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 0 days.

(21) Appl. No.: 15/039,788

(22) PCT Filed: Nov. 27, 2014

(86) PCT No.: PCT/EP2014/075763
§ 371 (c)(1),
(2) Date: May 26, 2016

(87) PCT Pub. No.: WO2015/082292
PCT Pub. Date: Jun. 11, 2015

(65) Prior Publication Data
US 2016/0377528 A1 Dec. 29, 2016

(30) Foreign Application Priority Data
Dec. 2, 2013 (FR) .................................. 13 61916

(51) Int. Cl.
G01N 21/17 (2006.01)
G01M 11/08 (2006.01)
(Continued)

(52) U.S. Cl.
CPC ..... *G01N 21/1702* (2013.01); *G01D 5/35316* (2013.01); *G01M 5/0008* (2013.01);
(Continued)

(58) Field of Classification Search
CPC ............... G01N 21/1702; G01N 29/07; G01N 29/2418; G01N 29/0672;
(Continued)

(56) References Cited

U.S. PATENT DOCUMENTS 4,697,926 A * 10/1987 Youngquist ........ G01D 5/35383
250/227.12
4,699,513 A * 10/1987 Brooks ................ G02B 6/2843
250/227.19
(Continued)

FOREIGN PATENT DOCUMENTS

EP 2 148 216 A2 1/2010
EP 2 549 247 A1 1/2013

OTHER PUBLICATIONS https://en.oxforddictionaries.com/definition/tomography.*
(Continued)

*Primary Examiner* — Mohamed K Amara
(74) *Attorney, Agent, or Firm* — Baker & Hostetler LLP

(57) ABSTRACT

A method and a device for analyzing a structure by tomography and diffuse acousto-elastic field correlation are provided. An optical fiber comprising a plurality of measurement points of FBG (Fiber Bragg Grating) type, comprising sensors of Bragg grating type, is deployed in or on the structure to be analyzed. The method comprises the emission of light, into the optical fiber, and the measurement by correlation for each pair of FBG sensors. In a development, a prior imaging of the structure is performed by reconstruction of the velocities of propagation. Other developments comprise: the determination of the positions of the FBG sensors, the calibration of the tomography, the rosette configuration of the sensors forming the measurement points, the use of a plurality of optical fibers, of multiplexers, of lasers, of optical circulators, of omnidirectional optical
(Continued)

sensors, of active noise sources, such as piezoelectric transducers, incorporated or not in the structure.

16 Claims, 6 Drawing Sheets

(51) Int. Cl.
  *G01N 29/06* (2006.01)
  *G01N 29/07* (2006.01)
  *G01N 29/24* (2006.01)
  *G01D 5/353* (2006.01)
  *G01M 5/00* (2006.01)
(52) U.S. Cl.
  CPC ........ *G01M 5/0016* (2013.01); *G01M 5/0025* (2013.01); *G01M 5/0091* (2013.01); *G01M 11/085* (2013.01); *G01N 29/0672* (2013.01); *G01N 29/07* (2013.01); *G01N 29/2418* (2013.01); *G01N 2021/1706* (2013.01); *G01N 2201/088* (2013.01); *G01N 2201/1211* (2013.01); *G01N 2291/011* (2013.01); *G01N 2291/2694* (2013.01)
(58) Field of Classification Search
  CPC ..... G01N 2291/2694; G01N 2201/088; G01N 2021/1706; G01N 2291/011; G01N 2201/1211; G01M 5/0016; G01M 5/0008; G01M 5/0091; G01M 5/0025; G01M 11/085; G01D 5/35316; G02B 6/00
  See application file for complete search history.

(56) References Cited

U.S. PATENT DOCUMENTS

| | | | | |
|---|---|---|---|---|
| 4,775,216 A * | 10/1988 | Layton | ............... | G01D 5/35383 250/227.12 |
| 4,778,248 A * | 10/1988 | Arzur | ................... | G02B 26/04 250/227.21 |
| 4,889,986 A * | 12/1989 | Kersey | ............... | G01D 5/35383 250/227.19 |
| 5,000,568 A * | 3/1991 | Trutna, Jr. | ......... | G01M 11/3118 250/227.15 |
| 5,111,466 A * | 5/1992 | Normandin | ........... | G01J 3/0259 356/326 |
| 5,144,690 A * | 9/1992 | Domash | ............. | G01D 5/35383 385/12 |
| 5,323,404 A * | 6/1994 | Grubb | .................. | H01S 3/0675 359/334 |
| 5,404,743 A * | 4/1995 | Froggatt | ................. | G01L 5/246 73/1.08 |
| 5,436,988 A * | 7/1995 | Narendran | ........... | G02B 6/3604 385/12 |
| 5,983,701 A * | 11/1999 | Hassani | ................. | G01N 3/307 73/12.01 |
| 6,285,806 B1 * | 9/2001 | Kersey | ............... | G01D 5/35383 385/12 |
| 6,376,830 B1 * | 4/2002 | Froggatt | ............ | G01M 11/3145 250/226 |
| 6,385,369 B1 * | 5/2002 | Hill | .................... | G02B 6/02138 359/489.03 |
| 6,630,658 B1 * | 10/2003 | Bohnert | ................ | G01L 11/025 250/227.14 |
| 6,856,400 B1 * | 2/2005 | Froggatt | ............. | G01M 11/331 356/477 |
| 7,388,673 B2 * | 6/2008 | Froggatt | .................. | G01J 9/02 356/451 |
| 7,480,056 B2 * | 1/2009 | Waagaard | .......... | G01D 5/35383 356/478 |
| 7,515,276 B2 * | 4/2009 | Froggatt | ............ | G01M 11/3172 356/497 |
| 7,948,633 B2 * | 5/2011 | Froggatt | ............ | G01M 11/3172 356/479 |
| 8,035,393 B2 * | 10/2011 | Tenghamn | ............. | G01V 3/083 324/347 |
| 8,208,767 B2 * | 6/2012 | Duncan | ................... | E21B 47/06 250/227.18 |
| 8,234,924 B2 * | 8/2012 | Saxena | .................. | G01N 29/11 385/13 |
| 8,537,367 B2 * | 9/2013 | Froggatt | ................ | G01M 11/35 356/466 |
| 8,964,172 B1 * | 2/2015 | Breiholz | .............. | G01M 11/086 250/227.14 |
| 9,158,054 B2 * | 10/2015 | Giurgiutiu | ............... | G02B 6/00 |
| 9,429,696 B2 * | 8/2016 | Donhowe | .......... | A61B 1/00167 |
| 9,488,786 B2 * | 11/2016 | Koste | ................. | G01D 5/35358 |
| 9,726,645 B2 * | 8/2017 | Soejima | ............ | G01N 29/2418 |
| 9,733,120 B2 * | 8/2017 | Stokely | .................. | G01H 9/004 |
| 2002/0041733 A1 * | 4/2002 | Mihailov | .......... | G02B 6/02138 385/37 |
| 2004/0202400 A1 * | 10/2004 | Kochergin | ......... | G01D 5/35316 385/12 |
| 2005/0131289 A1 * | 6/2005 | Aharoni | ............. | A61B 5/02007 600/407 |
| 2007/0266788 A1 * | 11/2007 | Kim | .................... | G01M 5/0033 73/588 |
| 2008/0156971 A1 | 7/2008 | Ogisu et al. | | |
| 2008/0212082 A1 * | 9/2008 | Froggatt | ............. | G01M 11/083 356/73.1 |
| 2009/0157358 A1 * | 6/2009 | Kim | ......................... | G01L 1/16 702/185 |
| 2011/0222062 A1 * | 9/2011 | Martini | .................. | G01N 21/05 356/417 |
| 2011/0228255 A1 * | 9/2011 | Li | .......................... | G01B 11/18 356/33 |
| 2014/0131562 A1 * | 5/2014 | Song | ...................... | G01H 9/004 250/227.18 |
| 2014/0152995 A1 * | 6/2014 | Dong | ......................... | G01L 1/246 356/477 |
| 2016/0138909 A1 * | 5/2016 | Wakahara | .............. | G01B 11/18 73/800 |
| 2016/0274064 A1 * | 9/2016 | Wysocki | ........... | G01N 29/2418 |
| 2017/0219208 A1 * | 8/2017 | Song | ......................... | F23N 5/16 |

OTHER PUBLICATIONS

A. Duroux et al., "Extracting guided waves from cross-correlations of elastic diffuse fields: Applications to remote structural health monitoring," Journal of Acoustical Society of America, vol. 127, No. 1, Jan. 2010, pp. 204-2155, XP012135139.
G. Kahandawa et al., "Use of FBG sensors in SHM of Aerospace structures," Third Asia Pacific Optical Sensors Conference, vol. 8351, No. 1, Jan. 31, 2012, pp. 1-10, XP060001193.
Y. Botsev et al., "Using Fiber Bragg Gratings to Measure Lamb Waves in an Anisotropic Composite Plate," 19th International Conference on Optical Fibre Sensors, Proceedings of SPIE, vol. 7004, Jan. 1, 2008, pp. 700445-1-700445-4, XP002728264.
N. Takeda et al., "Development of smart composite structures with small-diameter fiber Bragg grating sensors for damage detection: Quantitative evaluation of delamination length in CFRP laminates using Lamp wave sensing," Composite Science and Technology, vol. 65, No. 15-16, Dec. 1, 2005, pp. 2575-2587, XP027688113.

* cited by examiner

TESTING OF AN INDUSTRIAL STRUCTURE

CROSS-REFERENCE TO RELATED APPLICATIONS

This application is a National Stage of International patent application PCT/EP2014/075763, filed on Nov. 27, 2014, which claims priority to foreign French patent application No. FR 1361916, filed on Dec. 2, 2013, the disclosures of which are incorporated by reference in their entirety.

FIELD OF THE INVENTION

The invention relates to the field of metrology and in particular that of checking the health of structures by means of optical fibers.

BACKGROUND

The checking of the integrity of the structures (works of art, airplanes or pipe-lines for example) during their life is done generally during maintenance operations, with human inspection and intervention. Concrete technical problems consists for example in detecting and dimensioning a corroded zone on an airplane fuselage.

For these integrity checks, so-called non-destructive testing (NDT) methods are generally used, by so-called "conventional" methods (ultrasound, electromagnetic methods, etc.).

For a number of years now there have been research developments aiming to incorporate sensors in the structure at key points of the structures, and do so in order to automate the measurements (for example at regular intervals, these intervals being generally close together in time) and to be able to access information on the state of health for certain inaccessible zones, without dismantling or interrupting the operation of the structure. In general, these developments aim to space apart the maintenance intervals and therefore save money.

In particular, some research provides for the use of guided ultrasound waves (GW) emitted and detected by piezoelectric transducers (for example of PZT type) in-corporated in the structure. These guided waves are propagated over a great distance (some tens of cm to some hundreds of meters in highly favorable geometries such as pipelines), so that a limited number of transducers makes it possible to test a large area. Other technologies can be used to emit and/or detect the guided ultrasound waves (in addition to the optical fibers, PVDF films or magnetostrictive sensors for example).

One general technical problem lies in finding an acceptable trade-off between the number of sensors to be incorporated (cost, bulk, weight, etc.) and the quality of the information that can be recovered by these sensors. A high number of sensors means a high cost and a low number of sensors often means a lack of reliability of the information, risks of false alarms, or even a lack of redundancy in the event of failure of a sensor. The multiplication of the sensors however poses other specific problems (for example each incorporated sensor can constitute an additional point of embrittlement, which could risk inducing new defects in the structure). For each sensor, it is also essential to provide electrical power supply wires, which is not always possible. In industrial practice, very few applications provide a satisfactory trade-off.

Regarding the nature of the sensors, the solutions known from the prior art using lasers as measurement systems cannot be used in all circumstances. In particular, the lasers cannot be incorporated in the structures.

Some known approaches consist in proceeding with a reference measurement of the structure in the healthy state in order to observe a difference with a subsequent state to reveal the presence of the defect. In order to reliabilize this operation, various signal processing techniques exist, in particular for neutralizing the influence of temperature, but none is truly effective. In all cases, the interpretation of the signals remains very difficult.

The various aspects of the invention mitigate these drawbacks, at least partly.

SUMMARY OF THE INVENTION

Some embodiments of the invention advantageously provide for the use of Bragg gratings, notably of "FBG sensors" or "FBG measurement points", "FBG" being the acronym for "fiber Bragg grating".

A Bragg grating (or distributed Bragg reflector) is a quality reflector used in waveguides, for example in optical fibers. It is a structure in which layers of two materials of different refracted indices alternate, which provokes a periodic variation of the effective refractive index in the guide. A Bragg grating is a submicronic modulation of the refractive index of the fiber core: a grating of a few millimeters thus comprises several thousands of pitches. From a functional point of view, it acts as a reflector for a fine spectral band centered at a characteristic wavelength proportional to the pitch and to the index of the fiber core. Thus, any modification of these parameters displaces the Bragg wavelength proportionally. The tracking of its spectral displacements makes it possible to track back to the inducing parameters such as the temperature or the de-formations locally undergone by the optical fiber. These Bragg gratings are produced by laser in a single-mode fiber core. The inscription of these gratings can notably be performed by transverse insolation with an interference figure created by two laser beams.

According to one embodiment, there is disclosed a method for analyzing a structure by diffuse field correlation, an optical fiber comprising a plurality of measurement points, a measurement point comprising sensors of fiber Bragg grating (FBG) type, the optical fiber being deployed "in" (for example "placed a posteriori" or "natively integrated in") or "on" (for example "placed on" or "attached" or "associated with") the structure to be analyzed, the method comprising the emission of light into the optical fiber; and the measurement by correlation for at least some of the pairs of FBG sensors of the acousto-elastic field being propagated "in" (or "within", "through", "via") the structure. The FBG sensors or pairs of sensors can be interrogated substantially simultaneously. "Substantially" refers to the velocity of the elastic waves and to the fact that metrologically the interrogations take place within a time difference (time intervals close together to obtain meaningful measurements from the point of view of the propagation of the elastic waves in the structure). All or some of the sensors can be interrogated, according to various implementations. A subset of sensors can be interrogated substantially simultaneously, while another subset can be the subject of a delayed interrogation (for example sequentially or parallel in pairs or even combining these interrogation modes, by rotation, etc.). The acousto-elastic field denotes the field of the mechanical waves (sounds, ultrasounds, etc.) which are propagated in a solid medium. Unlike the case of fluid, there are two types of acoustic waves for a solid material. These waves are better known as elastic (shear and compression-traction) waves. The acoustoelastic effect reflects a dependency of the velocity of propagation of the acoustic waves as a function of the state of deformation of the solid. The structure to be analyzed does not have any particular restrictions in as much as any type of structure (in particular industrial) can be analyzed by the methods and systems described herein.

In a development, the method further comprises a step of reconstruction of the velocities of propagation by tomography, the imaging being performed by reversal of all the times of flight between the FGB sensors, each time of flight for each pair of FBG sensors being deduced from the correlation measurement. This development is optional. It offers the advantage of improved subsequent interpretation.

In a development, the position in space of each measurement point is previously and individually measured. This solution presents the advantage of simplicity of implementation.

In a development, the temperature of the structure is measured and a variation of time of flight induced by a change of temperature is compensated. The temperature can in fact influence the times of flight and it is good to be able to correct or compensate the thermal effects. Physically, a thermocouple can be used but other measurement methods are possible.

In a development, the imaging of the structure by tomography is performed by the measurement of at least two times of flight, a first measurement being performed in an initial or reference state and a second measurement being performed in a subsequent state (for the same pairs of measurement points). The subsequent state is called "current", it therefore corresponds to the present time of the measurement ("second set of measurements").

The implementation of a tomography (entirely optional) on the data deriving from the first measurement makes it possible in particular to identify certain geometrical peculiarities of the structure. This corresponds to a static measurement done in the initial (or reference) state. The imaging of the structure at rest can optionally be subtracted from subsequent images of the structure (subtraction of pixels, as regards image content). In other words, this optional mapping makes it possible to identify certain geometrical peculiarities of the structure in order to not confuse them with defects on the mappings obtained on the second measurement set.

In a development, the method further comprises a second measurement performed in a subsequent state for the same pairs of measurement points as the first measurement and further comprises a mapping by tomography of the variations of velocities of propagation in the structure between the initial state and the subsequent state obtained from differences in the times of flight measured between the two states. In other words, the variation of the times of flight (measured for the pairs) are measured between the two states. This makes it possible to obtain, by tomography, a mapping of the variations of velocity of propagation on the elastic (elasto-acoustic) waves between the instant of the measurement associated with the current (present) state and the instant associated with the reference state. For example, between the instant t of the measurement and the initial instant $t_0$, it can be seen that the waves goes "more slowly" (respectively "more quickly") at certain points and deduce therefrom the identification of the defects or the damage sustained in the structure.

In a development, a measurement point comprises an FBG sensor. The use of a sensor of this type to do the diffuse field correlation has not been described a priori. In another development, a measurement point comprises three receiving and directional FBG sensors arranged substantially at 120° to one another in a so-called rosette configuration. The rosette configuration is the trade-off which minimizes the number of hardware elements while ensuring a good measurement quality. A measurement point can also comprise any number of FBG sensors (for example 5 sensors, 6 sensors, etc.).

In a development, the measurement by correlation comprises a coda correlation of correlations between FBG sensors. This entirely optional development optimizes the device, since it makes the arranging of the optical fiber on the structure easier. Consequently, the times needed to install can be reduced, the measurement point positioning errors minimized, etc. The "coda correlation of correlations" consists, for a pair of measurement points A and B, in choosing any measurement point $C_i$ selected from all the measurement points (except A and B); in correlating the measurements for each of the points A and B with this any measurement point $C_i$; in correlating the coda of these correlations to obtain the correlation between the measurement points A and B. It is possible to repeat the operation for some or all of the possible measurement points $C_i$ and to aggregate the correlations obtained to obtain a correlation between A and B with a better reliability. All this can be applied to all or some of the possible pairs of FBG sensors.

In a development, there is disclosed the use of a plurality of optical fibers, each comprising (at least partially FBG sensors). The implementations in practice can vary. Each sensor or pair of sensors can be interrogated separately.

There is also disclosed a system for analyzing a structure, comprising at least one optical fiber comprising a plurality of measurement points, a measurement point comprising one or more sensors of fiber Bragg grating (FBG) type; a light source coupled to the optical fiber; a photo detector or an optical spectrum analyzer for analyzing the reflected light at the end of its path in the optical fiber; and signal processing means for performing correlation and tomography computations.

In a development, the source of the light source is a laser for which the wave-length can be varied or a wide band optical source of determined reflected optical spectrum. The lasers are now commonplace and the associated measurements are efficient.

In a development, the optical fibers can be multiplexed by means, for example, of optical circulators and/or of spectrum analyzers and/or of multiplexers.

In a development, the unidirectional sensors of FBG type are complemented or replaced by omnidirectional sensors of FOD (Doppler effect-based fiber optic) type. The sensors can therefore all be of FBG type, or all of FOD type, or even the method can be implemented on a system comprising both types of sensors simultaneously (in variable proportions, versus economic and performance aspects).

In a development, the system further comprises one or more active noise sources positioned in or on the structure so as to obtain a diffuse acousto-elastic field, that is to say one that best observes the characteristics of the diffuse field. In one implementation, said placement or positioning is interactively guided by the current measurements. In another implementation, the location of the noise sources is determined theoretically (that is to say "predetermined"). In another implementation, an indication is returned as to the appropriateness of said positioning (versus the diffuse field hypothesis). In another implementation, the multiplicity of the noise points or sources (combined with placements performed randomly) tends to guarantee the obtaining of a diffuse field (without return loop, i.e. a priori). In other words a system is disclosed that comprises one or more active noise sources which can be used to complement or replace the natural noise sources present in the structure, which can also be advantageous for the calibration. These additional sources can be, for example, piezoelectric transducers shrewdly placed in the structure, in order to be able to take measurements when desired (for example, in an airplane if the natural sources are turbulences in flight, it will advantageously make use of additional active sources to be able to perform a measurement on the ground, when there is no longer any "natural" noise in the structure). These sources will advantageously be placed so as to create an acoustic field which best observes the condition of equidistribution in energy. For example, to satisfy this condition, the sources can be placed close to natural diffusers (or even around the zone to be tested). It is possible to use active sources incorporated in the structure. It is also possible to use active sources which are not incorporated therein: for example, a jet of compressed air whose contact zone randomly sweeps the structure to be examined (so as to satisfy the condition of equidistribution in energy). The system can therefore comprise at least one noise source, said source being for example a jet of compressed air whose contact zone randomly sweeps the structure.

In a development, an active noise source can be a piezoelectric transducer, possibly of PZT type.

According to an aspect of the invention, a large number of measurement points is advantageously used in combination with a measurement by correlation of the diffuse field, which has never been done with FBG sensors, in order to produce the tomography.

According to a particular embodiment of the invention, the structure to be examined is "imaged". This imaging allows for easier interpretations than those evolving from the analysis of raw signals, since the geometrical singularities of the structure appear in a visual form and are not confused with a defect. In some embodiments, the reference state is then no longer needed.

Industrial structures are often very complex geometrically (because of stiffeners, rivets, bondings, etc.) and so a multitude of ultrasound echos appear. An imaging therefore considerably aids in the interpretation of the signals.

Moreover, a multiplicity of sensors increases the resolution of the imaging and therefore reinforces the advantages of the invention.

Advantageously, the bulk of the gear according to the invention remains limited, even with many sensors, which allows for relatively portability, compatibility and usefulness with regard to the constraints of an integrated structural health monitoring (SHM) system.

The measurements are performed passively, that is to say without the emission of acoustic waves. Consequently, the energy consumption is reduced and allows for embedded solutions (for example onboard an airplane, a boat or on the seabed).

The method produces a mapping of the zone to be tested that can easily be interpreted (which limits the risks of false alarms). The method is all the more effective when the acoustic field is diffused, that is to say geometrical elements diffract the acoustic field multiple times, which is particularly true in the industrial structures which are never simple plates but typically include stiffeners, rivets or even local overthicknesses which diffract the waves and reinforce the diffuse nature of the field.

The bulk is reduced, compatible with incorporation of the gear in the structures to be monitored. For example, for incorporation in composite materials, whereas the use of piezoelectric transducers generally requires two electric wires per piezoelectric transducer, a single optical fiber incorporated between the plies of composites comprises tens of measurement points. The number of input points in the structure is therefore very limited which limits the potential embrittlement points all the more.

Thus, the invention will be applicable for integrated structural health monitoring (SHM) operations, such as for example for the detection (and the characterization) of corrosion on an airplane fuselage, delamination in composite structures, corrosion or deposition in pipes.

The advantages linked to the embodiments and the use of optical fibers comprise small bulk, reduced weight, great bandwidth, significant distancing, electromagnetic immunity, good resistance to severe or ionizing radiations, among others.

DESCRIPTION OF THE FIGURES

Different aspects and advantages of the invention will become apparent from the description of a preferred but nonlimiting implementation of the invention with reference to the figures below.

DETAILED DESCRIPTION OF THE INVENTION

The invention can advantageously use a large number of measurement points to be able to do the tomography by guided waves. For that, one or more optical fibers on which are etched bragg gratings (FBG) are incorporated in (or glued on) the structure. A single optical fiber can comprise tens of FBGs, and therefore as many measurement points. The bulk is therefore reduced.

However, the FBGs can operate only as waveguide receiver but not as emitter. The current SHM systems based on FBGs therefore use piezoelectric transducers also as emitter. To do the tomography, there would need to be one piezoelectric transducer for each FBG, therefore still a large number of piezoelectric transducers.

According to an embodiment of the invention, a technique is described which makes it possible to provide images of structures of industrial type over localized zones and/or of limited thickness (geometry of plate or tube type). The images can notably indicate the velocities of propagation of the guided waves. According to some implementations of the invention, this supply of images is done passively (i.e. without the emission of ultrasound waves by the embedded system).

The method notably comprises:

an ultrasound field measurement passively, by a diffuse field correlation technique, a technique deriving from geophysics, and recently studied in the context of integrated health monitoring. This type of measurement has never been performed with optical fibers provided with bragg gratings (FBG) as sensors. Now, it happens that the fiber bragg gratings (FBG) advantageously make it possible to have a large number of measurement points, a structure imaging by tomography performed by guided waves and which exploits the presence of this large number of measurement points. Such imaging is known from the prior art but only with the use of "active" measurements, that is to say measurements requiring the use of ultrasound wave emitter (for plates or for pipes).

Some embodiments of the invention provide for the use of FBG sensors, instead of the piezoelectric transducers usually used in the SHM systems.

The switch from piezoelectric transducers (for example of PZT type) to FBG sensors (or measurement points) is not obvious because these are two very different and non-interchangeable technologies. The piezoelectric transducers can be used both as emitters and as receivers while the FBGs can be used only as receivers. Moreover, the piezoelectric transducers are omnidirectional whereas the FBGs are directional. Finally, the setups are specific in both cases (electrical versus optical). The piezoelectric transducers and the FBGs are often presented as complementary to one another (piezoelectric transducer emission and FGB in reception) and the current SHM systems based on FGBs all use piezoelectric transducers incorporated in or placed on the structure with the optical fiber as acoustic wave emitter.

Figure 1:
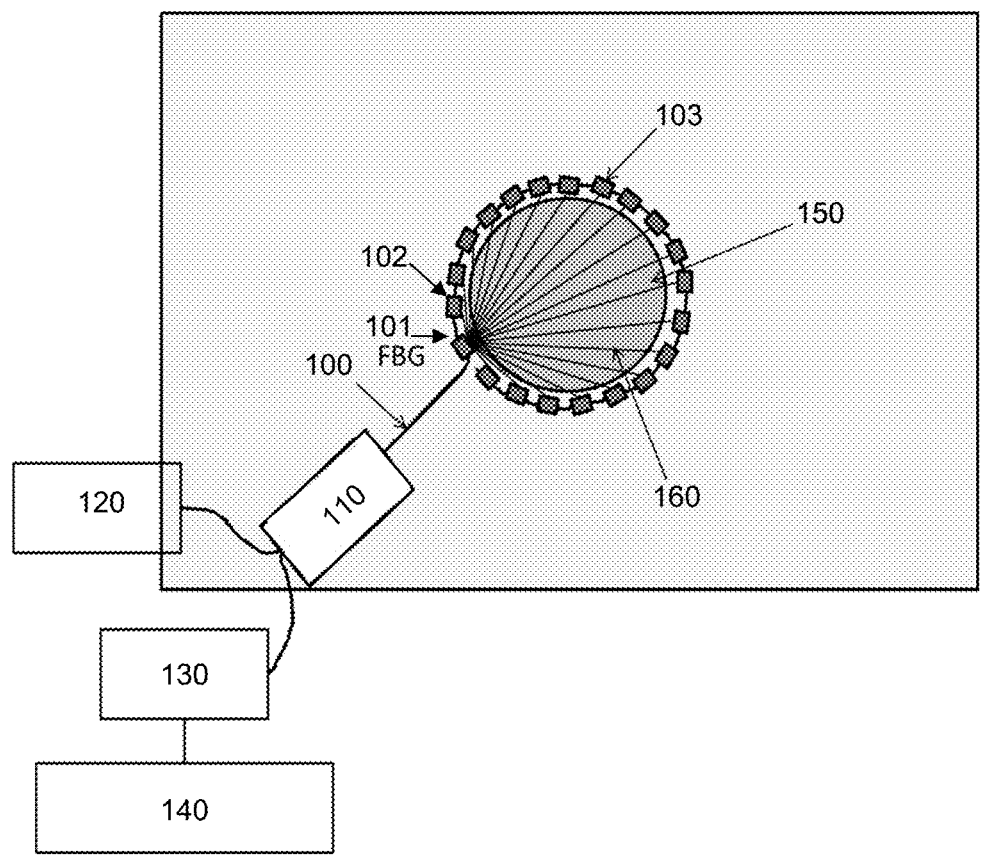
FIG. 1 shows the diagram of an exemplary device according to the invention.
Figure 4:
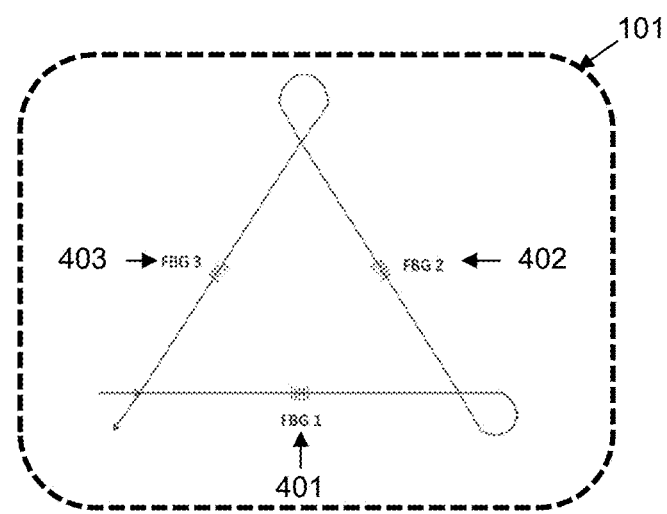
FIG. 4 illustrates an exemplary configuration of the FBG sensors according to a so-called "rosette" form.

FIG. 1 shows a possible diagram according to an exemplary embodiment of the device according to the invention. In the example, the device consists of an optical fiber 100 incorporated in a structure to be studied (or glued onto its surface) and which comprises a certain number of fiber bragg gratings (FBG), such as, for example, the measurement point FBG 101, or even FBG 102. The measurement points are represented by small rectangles. FIG. 4 details a possible configuration of a measurement point by FBG (so-called "rosette" configuration). A same optical fiber generally comprises some tens of FBG measurement points per fiber, even a few hundred. The optical fiber is incorporated in or glued or placed on or attached to or associated with the structure.

According to another embodiment of the invention, a number of optical fibers can be used. In this case, these fibers are integrated separately by means of a multiplexer.

The optical fiber 100 is coupled by a coupler 110 to a light source 120 (laser or wideband), which will emit into the fiber, and to a photodetector or an optical spectrum analyzer 130 which will analyze the reflected light at the end of its path in the optical fiber, itself connected to a digital processing unit (140). The different acoustic paths in the zone to be inspected 150 passing through the FGB measurement point 101 and each of the other measurement points is illustrated by the acoustic paths 160.

There are at least two possibilities for measuring the guided waves by using FBG measurement points. A first embodiment uses a laser for which the wavelength is varied. A second embodiment uses a wideband optical source for which the reflected optical spectrum is determined. The first embodiment offers the advantage of enhanced sensitivity. The second embodiment offers the advantage of a cost saving.

According to variant embodiments, the coupler 110 can be replaced by an optical circulator (not represented) and the spectrum analyzer (costly equipment item) or the photodetector 130 by FBGs arranged on multiplexed optical fibers (configuration often referred to as High-Speed Optical Wavelength Interrogation System). Other systems for the implementation of multiplexed optical fibers exist.

Figure 2:
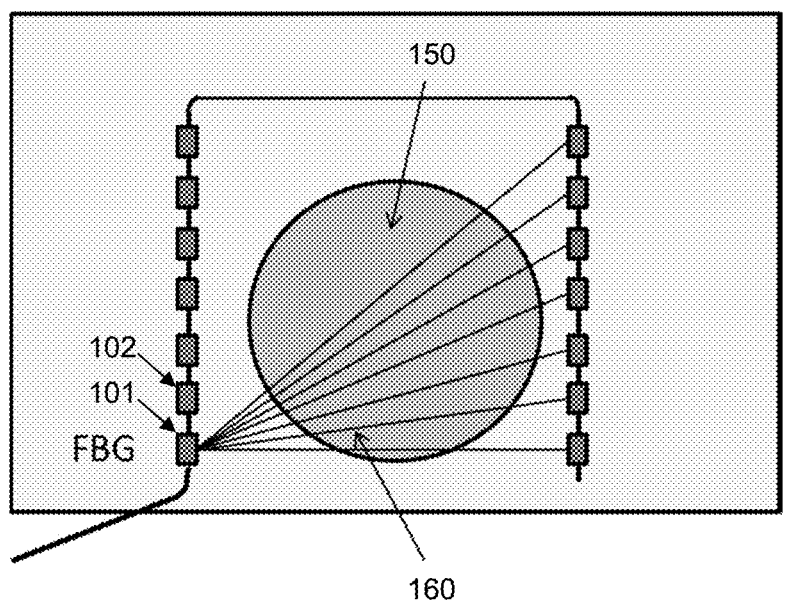
FIG. 2 illustrates another exemplary configuration of the measurement points according to the invention.

FIG. 2 illustrates another exemplary configuration of the measurement points according to the invention. The FBG measurement points (101, 102, . . . ) can be arranged in different ways all around the zone to be inspected 150. FIG. 2 illustrates another spatial configuration of the optical fiber 100 bearing the FBGs 101, 102, etc. The limitations on the different configurations in terms of arrangement and number of measurement points are only those which stem from the efficiency of subsequent re-construction, by means of the tomography algorithm chosen for the defect that is to be studied.

Figure 3A:
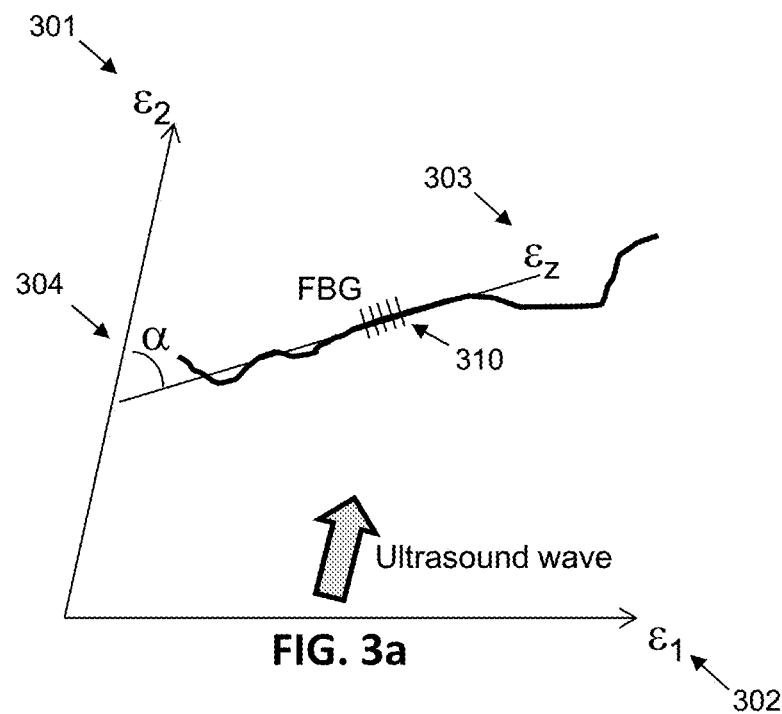
FIGS. 3a and 3b illustrate an example of amplitude measurement as a function of angle of incidence on a sensor.
Figure 3B:
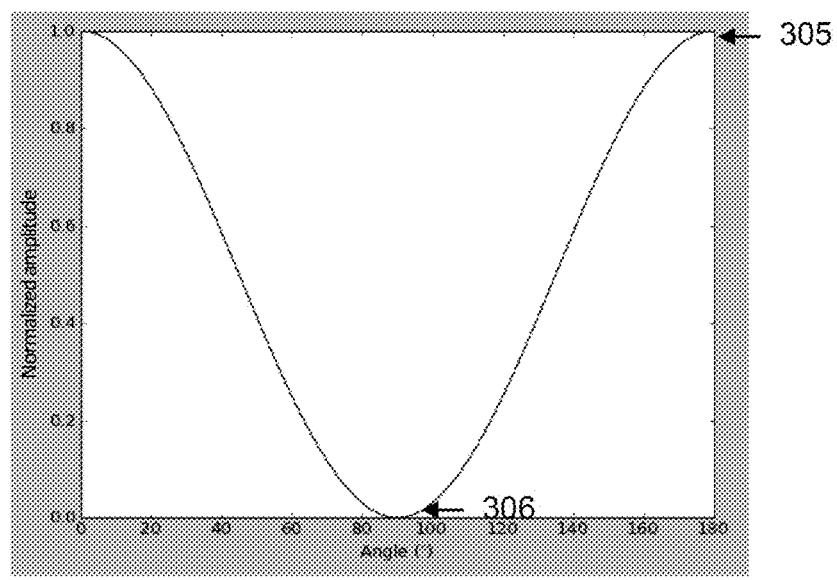

FIGS. 3a and 3b illustrates an exemplary measurement of amplitude as a function of angle of incidence on a sensor. The FGBs per se are directional sensors: the measured amplitude depends on the angle of incidence of the wave on the sensor (FIG. 3a). The fiber 100 comprises an FBG sensor 310 oriented according to an alpha angle 304, exposed to a wave in a direction 301 (of perpendicular 302): the amplitude is maximum (305) when the FBG is in the direction of propagation of the wave and zero or minimum (306) when it is orthogonal thereto (FIG. 3b).

With the FBGs being etched in the axis of the optical fiber, if the arrangement presented in FIGS. 1 and 2 corresponded to the real orientation of the FBGs, the measured amplitude would be practically zero for all the pairs of FBGs of interest, that is to say for those whose acoustic path passes through the core of the zone to be inspected. In a particular embodiment of the invention, sensors for optical fiber of omnidirectional type (for example of "FOD", Doppler effect-based fiber optic, type) are used (instead of or complementing the FBG sensors).

In another embodiment, a so-called "rosette" configuration is used, illustrated in FIG. 4. The figure shows the detail of the arrangement of each measurement point, for example the FBG measurement point 101, the different measurement points being represented by rectangles in FIGS. 1 and 2. Each measurement point comprises three FBG gratings arranged at 120° to one another (FBG 1 401, FBG 2 402, FBG 3 403). Because of this spatial configuration, for each pair of measurement points, the correlation is performed between the two FBGs (one for each measurement point) which are best aligned.

Figure 5A:
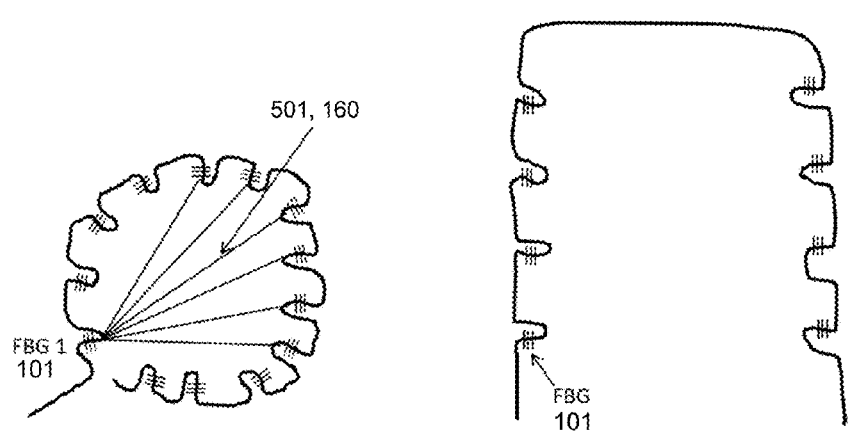
FIGS. 5a and 5b illustrate another exemplary configuration of the optical fiber according to the invention, arranged in "meander-fashion"

According to a variant illustrated in FIG. 5a, the optical fiber 100 can be arranged in "meander fashion". In this configuration, fewer paths are then available for the tomography (the only ones that can be used are those for which the FBGs are relatively well aligned, in the figure, the paths marked 501).

For each pair (A, B) of measurement points of this grating, a correlation of the acoustic field u measured simultaneously over a long period at A and at B is performed, for example by applying (there are other computation possibilities):

$$C_{AB}(t) = \int u_A(t+\tau) \cdot u_B(\tau) d\tau.$$

It is established that the correlation (strictly speaking, its derivative) converges toward the Green function between A and B if the different components of the wave field observe the condition of equi-distribution in energy (the phase and amplitude distribution of the waves is random, so-called "diffuse field" hypothesis). The Green function between A and B is the recording that would be obtained at A if a source emitted a Dirac at B.

The conditions of equi-distribution energy can be obtained when the sources are randomly distributed in the medium or when the number and the distribution of the sources is limited but the medium is highly diffusive. Experimental demonstrations have shown that the convergence was obtained in frequency ranges advantageous for SHM (i.e. from a kilohertz to a few megahertz).

For example, the natural noise sources in the industrial structures can be those associated with the turbulent limit layer in aeronautics, the wave impact, the vibrations induced by the engines on a boat or a turbulent flow in a tube.

Figure 5B:
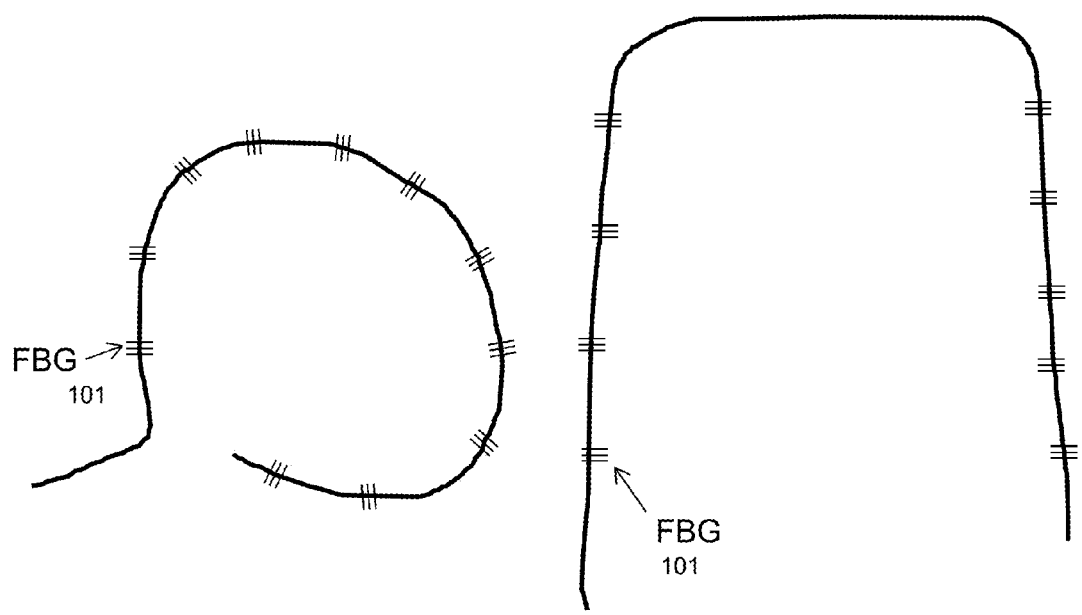

According to a variant illustration in FIG. 5b, the optical fiber can be arranged without particular meanders (which can be easier or feasible in some situations). One way to remedy this relatively unfavorable geometry consists in proceeding with the coda correlation of correlations which amounts to involving, for each pair (A, B) of measurement points, at least one third measurement point C, and to carrying out the correlation $C_{AC}$ and $C_{BC}$ then the correlation of the coda of these two signals to obtain $C_{AB}$, this step being able, moreover, to be repeated for all the measurement points C different from A and B then averaged in order to improve the signal-to-noise ratio. This implementation requires a simplified arrangement of the fiber, which no longer requires meanders of the fiber to best align the FBGs relative to one another (FIG. 5b). On the other hand, the signal processing time is longer. In practice, this is done as follows: for the pair concerned (A, B), another measurement point $C_i$ out of all the available points is used. Initially, the signals measured between A and B on the one hand and $C_i$ on the other hand are correlated. Once the correlations $C_iA$ and $C_iB$ have been performed, the coda of these signals is correlated to obtain the correlation between A and B. Since this can be repeated over some or all of the measurement points $C_i$, the set of correlations obtained can be summed to obtain a better estimation of Green function between A and B.

From the Green function obtained by the correlation, the measurement of the time of flight between A and B is deduced. When repeated for all the possible pairs of receivers, this operation provides a large quantity of data in times of flight that can be exploited to perform a reconstruction by tomography in terms of velocity of propagation.

Figure 6:
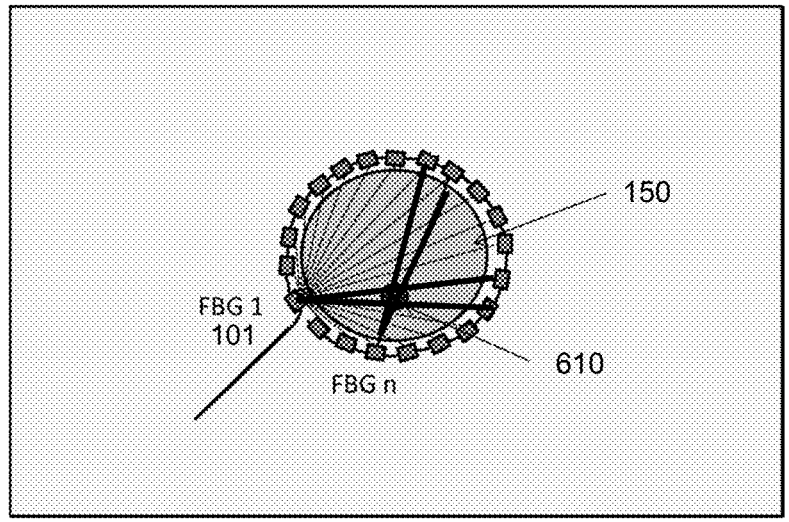
FIG. 6 illustrates an example for which acoustic rays are affected by a corroded zone.

FIG. 6 illustrates an example for which the acoustic rays are affected by a corroded zone 610 on a study zone 150. In the example, some acoustic rays passing through the FBG measurement points 1 101 (generally FBG n) are affected. Out of all the possible paths, only those passing through the corroded zone 610 (or subject to other damage such as delamination) are impacted (or affected, see the solid lines in the illustration), the other paths are unchanged (dotted lines).

The tomography method according to the invention reverses all of the measured times of flight, in order to reconstruct a map of velocities of propagation that are compatible with all the times of flight. For the guided waves, the velocity of propagation dependent on the thickness of the structure (by a known relationship, i.e. the scattering curves), this map of velocity of propagation can be transposed to a map of thickness if seeking to detect corrosion. This method also works, for example, for detecting the delamination of a composition structure (since, at the delamination, the velocity of the guided waves is also modified).

The map that is obtained is an image of the structure. This image can be interpreted: the extent of the damage zone is made visible. For corrosion damage, for example, it therefore becomes possible to know the extent and the residual thickness. Consequently, the seriousness of the damage can be assessed, in order, if necessary, to take corrective measures.

The obtaining of an image of the structure therefore makes it possible to detect one or more defects, without needing to subtract the signal measured at an instant t from that measured at an instant $t_0$, the reference state for which the structure is considered healthy. The previous provision of this reference state involves numerous constraints (for example, need to construct a database with measurements at all the temperatures that the structure have to be subjected to, problems in case of aging of the sensors resulting in false alarms, etc.).

Figure 7:
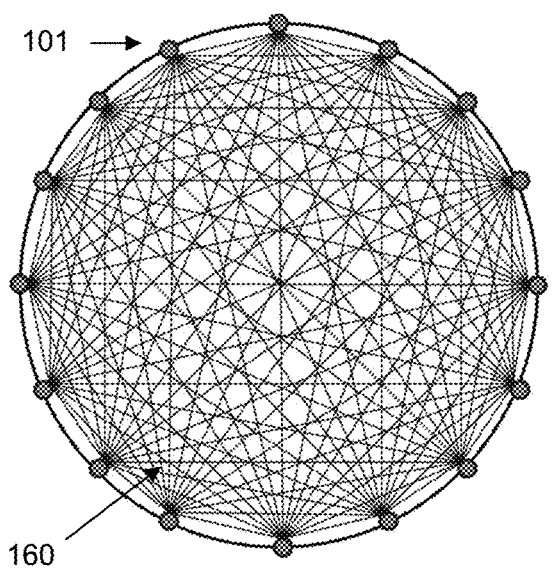
FIG. 7 illustrates the possible acoustic paths for an exemplary configuration with 16 sensors arranged in a circle.

FIG. 7 illustrates the possible acoustic paths for an exemplary configuration with 16 sensors (of type 101) arranged in a circle. The robustness of the method presented here stems from the number of measurement points and therefore from the number of possible paths. FIG. 7 presents the multiplicity of the acoustic paths 160 in the case of the use of 16 sensors or measurement points. It is possible to use hundreds of sensors.

Different embodiments are possible to implement the tomography, in particular as to the calibration of the method. Tomography presupposes accurately knowing the position of the FBGs.

According to one embodiment, the individual positions of the FBG measurement points are measured.

According to another embodiment, a calibration is performed just after the placement of the fiber, at a controlled temperature, in order to measure the times of flight between each of the pairs of FBGs. If the velocity is known, which is not always the case, it is possible to deduce the position of the FBGs with very good accuracy. Failing this, it is possible to measure the time of flight for each of the pairs of sensors and to establish a mapping of variation of the velocity of propagation relative to the initial state. Knowing the temperature at the time of calibration, if the temperature of the structure is known using an incorporated thermocoupler at the instant t it is also possible to neutralize the variation of time of flight induced by the temperature. Failing that, the temperature generally implies a uniform (although potentially anisotropic) effect whereas a defect will generally have a localized effect. The problems mentioned previously concerning the subtraction of the reference state are therefore less critical than in the current techniques and above all are neutralized by a large number of measurement points.

According to another embodiment, a mapping of the structure in a healthy state (reference state of the structure) is carried out. In this case, there is no need for subtraction of the signals. This mapping in the healthy state provides an image which makes it possible to identify certain geometrical peculiarities (such as rivets for example) within the zone to be tested in order to not identify them as defects in subsequent mappings.

According to an entirely optional variant, an attenuation tomography is performed. The correlation makes it possible to reconstruct not only the phase of the Green function but also its amplitude. An attenuation tomography can then be performed. The convergence of the correlation will be different and the directionality of the FBGs will be able to be neutralized. This configuration is advantageous in certain situations, particularly when the defect that is to be studied has little influence on the velocity of propagation of the ultrasound waves.

According to a development of the invention, the correlation between two FBGs situated on a same fiber can be performed. According to another development, a number of optical fibers are used, with correlation between two different FBGs situated on different fibers.

The present invention can be implemented from hardware and/or software elements. It can be available as computer program product on a computer-readable medium. The medium can be electronic, magnetic, optical or electromagnetic.

The invention claimed is:

1. A method for analyzing a structure by diffuse acousto-elastic field correlation using an optical fiber comprising a plurality of measurement points, a measurement point comprising one or more sensors of fiber Bragg grating FBG type, comprising a millemetric grating, the optical fiber being deployed in or on a structure to be analyzed, the method comprising:
    emitting light into the optical fiber;
    interrogating substantially simultaneously pairs of FBG sensors measuring, over time, acousto-elastic waves at one or more of the plurality of measurement points; and
    determining by correlation of acousto-elastic signals, for at least some of the pairs of FBG sensors, a Green function of the structure and said FBG sensors.

2. The method as claimed in claim 1, further comprising a step of reconstruction of velocities of propagation of the acousto-elastic waves by tomography, imaging being performed by reversal of all times of flight between the pairs of FBG sensors, each time of flight of the acousto-elastic waves propagating in the structure for each pair of FBG sensors being deduced from a correlation measurement, the FBG sensors of the pair of FBG sensors being associated with different measurement points.

3. The method as claimed in claim 2, wherein a position in space of each measurement point is previously and individually measured.

4. The method as claimed in claim 2, wherein a temperature of the structure is measured and a variation of time of flight induced by a change of temperature is compensated.

5. The method as claimed in claim 2, comprising a first measurement performed in an initial or reference state of the structure and comprising an imaging of the structure performed by tomography from said first measurement making it possible to identify certain geometrical peculiarities of the structure.

6. The method as claimed in claim 5, further comprising a second measurement performed in a subsequent state for the same pairs of measurement points as the first measurement and further comprising a mapping by tomography of variations of the velocities of propagation in the structure between the initial state and the subsequent state obtained from differences in times of flight measured between two states.

7. The method as claimed in claim 1, wherein a measurement point comprises an FBG sensor.

8. The method as claimed in claim 1, wherein a measurement point comprises three receiving and directional FBG sensors substantially arranged at 120° to one another in a rosette configuration.

9. The method as claimed in claim 1, wherein the measurement by correlation comprising a coda correlation of correlations between FBG sensors.

10. The method as claimed claim 1, comprising a plurality of optical fibers as claimed in claim 1, each FBG sensors being able to be interrogated separately.

11. A system for analyzing a structure, comprising:
    at least one optical fiber comprising a plurality of measurement points, a measurement point comprising one or more sensors of fiber Bragg grating FBG type, comprising a millimetric grating, said FBG being configured to measure substantially simultaneously, over time, acousto-elastic waves at one or more of the plurality of measurement points;
    a light source coupled to the at least one optical fiber;
    a photo detector or an optical spectrum analyzer to analyze a reflected light at an end of its path in the at least one optical fiber; and
    a digital processing unit configured to determine by correlation of acousto-elastic signals, for at least some pairs of FBG sensors, a Green function of the structure and said FBG sensors.

12. The system as claimed in claim 11, wherein the light source is a laser for which a wavelength is varied or a wide band optical source of determined reflected optical spectrum.

13. A system comprising a plurality of optical fibers as claimed in claim 11, the optical fibers being multiplexed by means of at least one optical circulator and/or one spectrum analyzer and/or one multiplexer.

14. The system as claimed in claim 11, wherein the one or more sensors of FBG type are unidirectional and are complemented by one or more omnidirectional sensors.

15. The system as claimed in claim 11, further comprising one or more active noise sources positioned in or on the structure so as to obtain a diffuse acousto-elastic field.

16. The system as claimed in claim 11, further comprising at least one active noise source that comprises a piezoelectric transducer.

* * * * *